Figure 1:
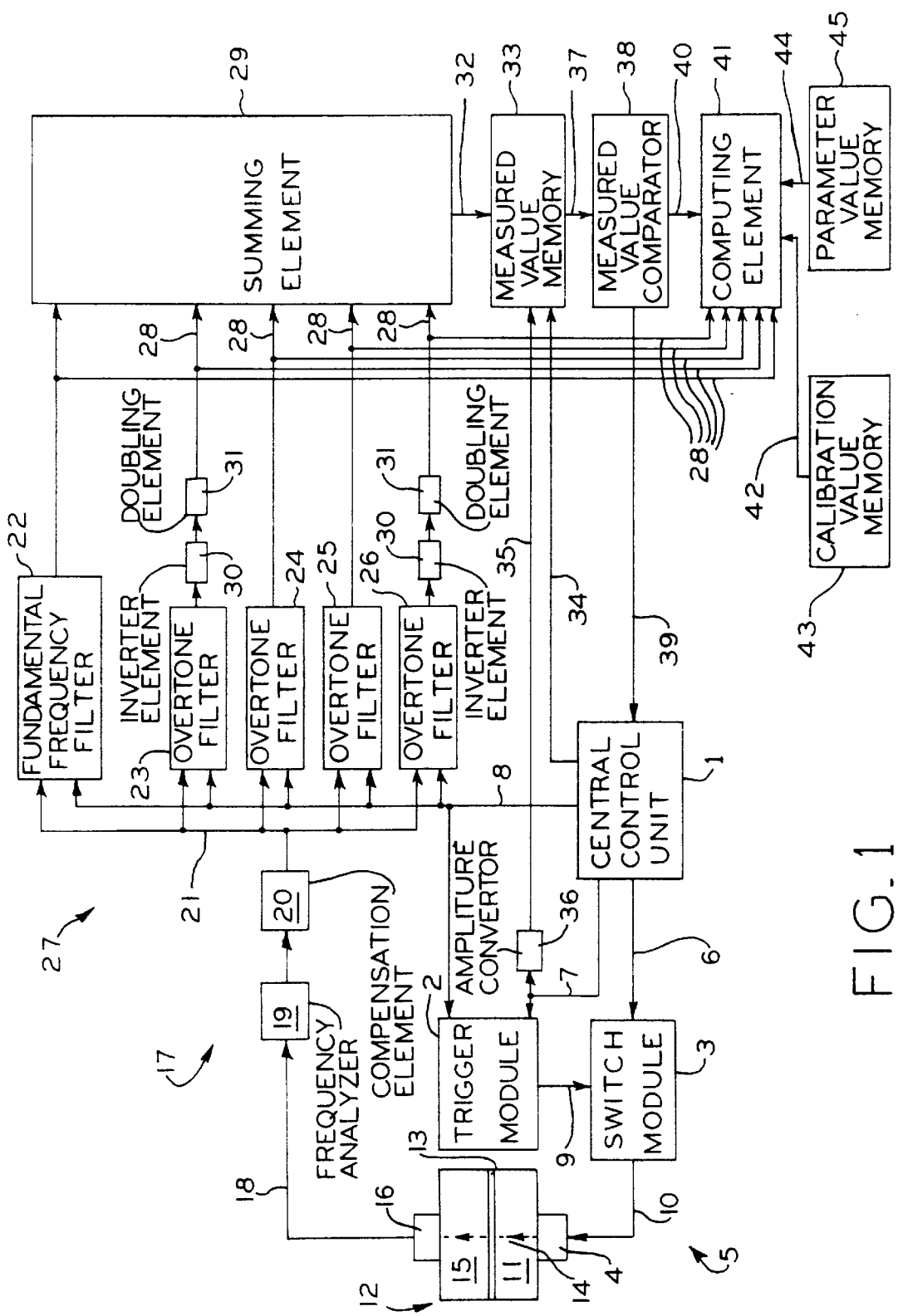

United States Patent [19]
Hirsekorn et al.

[11] Patent Number: 6,164,136
[45] Date of Patent: Dec. 26, 2000

[54] DEVICE FOR THE INVESTIGATION OF BOUNDARY LAYER AREAS USING ULTRASOUND

[75] Inventors: Sigrun Hirsekorn, Dudweiler; Silvia Fassbender, Saarbruecken, both of Germany

[73] Assignee: Fraunhofer-Gesellschaft zur Forderung der Angewandten Forschung E.V., Germany

[21] Appl. No.: 09/194,175
[22] PCT Filed: Mar. 6, 1998
[86] PCT No.: PCT/DE98/00673
§ 371 Date: Dec. 31, 1998
§ 102(e) Date: Dec. 31, 1998
[87] PCT Pub. No.: WO98/43110
PCT Pub. Date: Oct. 1, 1998

[30] Foreign Application Priority Data

Mar. 21, 1997 [DE] Germany ............... 197 11 863

[51] Int. Cl.[7] ................................. G01N 29/12
[52] U.S. Cl. ................................. 73/602; 73/579
[58] Field of Search ............... 73/579, 598, 597, 73/602, 582, 659

[56] References Cited

U.S. PATENT DOCUMENTS

| 4,539,847 | 9/1985 | Paap ............................ 73/579 |
|---|---|---|
| 4,566,330 | 1/1986 | Fujii et al. ..................... 73/599 |
| 4,662,222 | 5/1987 | Johnson ......................... 73/602 |
| 5,271,274 | 12/1993 | Khuri-Yakub et al. ........... 73/597 |
| 5,351,543 | 10/1994 | Migliori et al. ................. 73/579 |
| 5,635,644 | 6/1997 | Ishikawa et al. ................ 73/614 |
| 5,681,995 | 10/1997 | ooura et al. .................... 73/622 |

FOREIGN PATENT DOCUMENTS

| 0116901 | 8/1994 | European Pat. Off. . |
|---|---|---|
| 34 94 492 A1 | 8/1984 | Germany . |
| 31 48 735 C2 | 10/1986 | Germany . |
| 4324143 | 7/1994 | Germany . |

*Primary Examiner*—Hezron Williams
*Assistant Examiner*—Rose M. Miller
*Attorney, Agent, or Firm*—Baker & Daniels

[57] ABSTRACT

An apparatus for investigation of boundary lazier areas with ultrasound having at least one transmission unit with which transmission signals of adjustable amplitudes at one or more fundamental frequencies are generated. The apparatus also includes a receiving unit with which at least one fundamental frequency as well as the associated lowest harmonic of the fundamental frequency of the transmission signals can be detected and their frequency amplitudes can be detected. An analysis unit is provided in which the frequency amplitudes of the received signals can be combined into a measured value. The measured value has the simple frequency amplitude of a fundamental frequency and at least double the negative value of the frequency amplitude of the associated second harmonic of the fundamental frequency. By this means, an absolute measure of the cohesive force in the area of the investigated boundary layer area is generated.

14 Claims, 2 Drawing Sheets

DEVICE FOR THE INVESTIGATION OF BOUNDARY LAYER AREAS USING ULTRASOUND

The invention concerns a device for the investigation of boundary layer areas using ultrasound with at least one transmitting unit with which transmission signals of adjustable amplitudes with at least one fundamental frequency can be generated, with a receiver unit with which the at least one fundamental frequency as well as at least the associated lowest of the higher harmonics of the at least one fundamental frequency of the transmission signal can be detected in their frequency amplitudes as reception signals, and with an analysis unit in which the frequency amplitudes of the reception signals can be joined into a measured value.

A device of this type is known from German Patent No. 43 24 143 C1. In this device, a transmission unit is provided with which at a fundamental frequency, transmission signals of adjustable amplitude can be generated. With a receiver unit, frequency components at the fundamental frequency as well as higher harmonics of the fundamental frequency can be detected. A characterization of boundary layer areas with respect to cohesive force relationships in a boundary layer area being investigated is created through the frequency amplitudes of the fundamental frequency as well as at least one additional frequency amplitude at an additional frequency component which is related harmonically to the fundamental frequency are summed. In order to achieve physically correct relative measured values for characterizing the cohesive force potential, the frequency components at harmonics with an even ordinal number are to be weighted negatively and the harmonics with an uneven ordinal number are to be weighted positively. In addition, in order to correctly characterize the cohesive force potential in absolute terms as well, it is necessary to determine a direct current component.

While it is true that the cohesive force relationships can be characterized with the generic device it nevertheless has the disadvantage that the direct current component, by way of example, is technologically difficult to measure. In addition, quantitative statements with respect to the also important adhesive strength, i.e., the difference from maximum cohesive strength, is not possible.

The objective of the invention is to further develop a device of the type referred to at the beginning with which a precise, trouble-free determination of adhesive strength is created with low technological expenditure.

This objective is achieved according to the invention by the measured value having the simple frequency amplitude of a fundamental frequency and at least double the negative value of the frequency amplitude of the lowest of the higher harmonics associated with this fundamental frequency.

As a result of the measured value being composed of the simple frequency amplitude of the at least one fundamental frequency as well as at least double the negative value of the frequency amplitude of the associated lowest of the higher harmonics, i e., the second harmonic at double the fundamental frequency, quantitative statements on adhesive strength can be made which are relatively simple and free of interference. Determination of a direct current component is not necessary even for quantitatively correct adhesive force measured values.

In advantageous further developments, along with the second harmonic, also additional higher harmonics are measured. An increase in measuring precision, is achieved by this means. The frequency amplitudes of the third and fifth harmonics with respectively three times and five times the fundamental frequency are taken as simple positive values and that of the sixth harmonic with its sixfold fundamental frequency is taken as a double negative value. In this process, the fourth harmonic with the fourfold value of the fundamental frequency must be left out of consideration.

Accordingly, frequency components with the value of $(2n+1)$ times the fundamental frequency must be taken with a weight of one and those with the value of $2(2n+1)$ must be taken as a double negative value, whereby "n" represents a whole number equal to or larger than zero. Frequency components with the value of 4n times [the fundamental frequency] must be left out of consideration.

In addition, it is advantageous to provide transmission signals with at least two or more fundamental frequencies. By this means through nonlinear processes not only frequency components for fundamental frequencies as well as their associated higher harmonics, but also sum frequencies and difference frequencies of the various fundamental frequencies, higher harmonics, and combinations thereof can be generated and can be linked additively with in part simple positive weighting and in part double negative weighting.

For determining tensile adhesive strength, ultrasound waves with a large displacement component can be directed with the transmission device onto a test body perpendicularly to the surface, for example longitudinal waves perpendicularly striking a boundary layer area which is to be investigated, and for determining shear adhesive strength, ultrasound waves with a large displacement component can be directed parallel to the surface, for example transverse waves perpendicularly striking a boundary layer area which is to be investigated.

Figure 2:
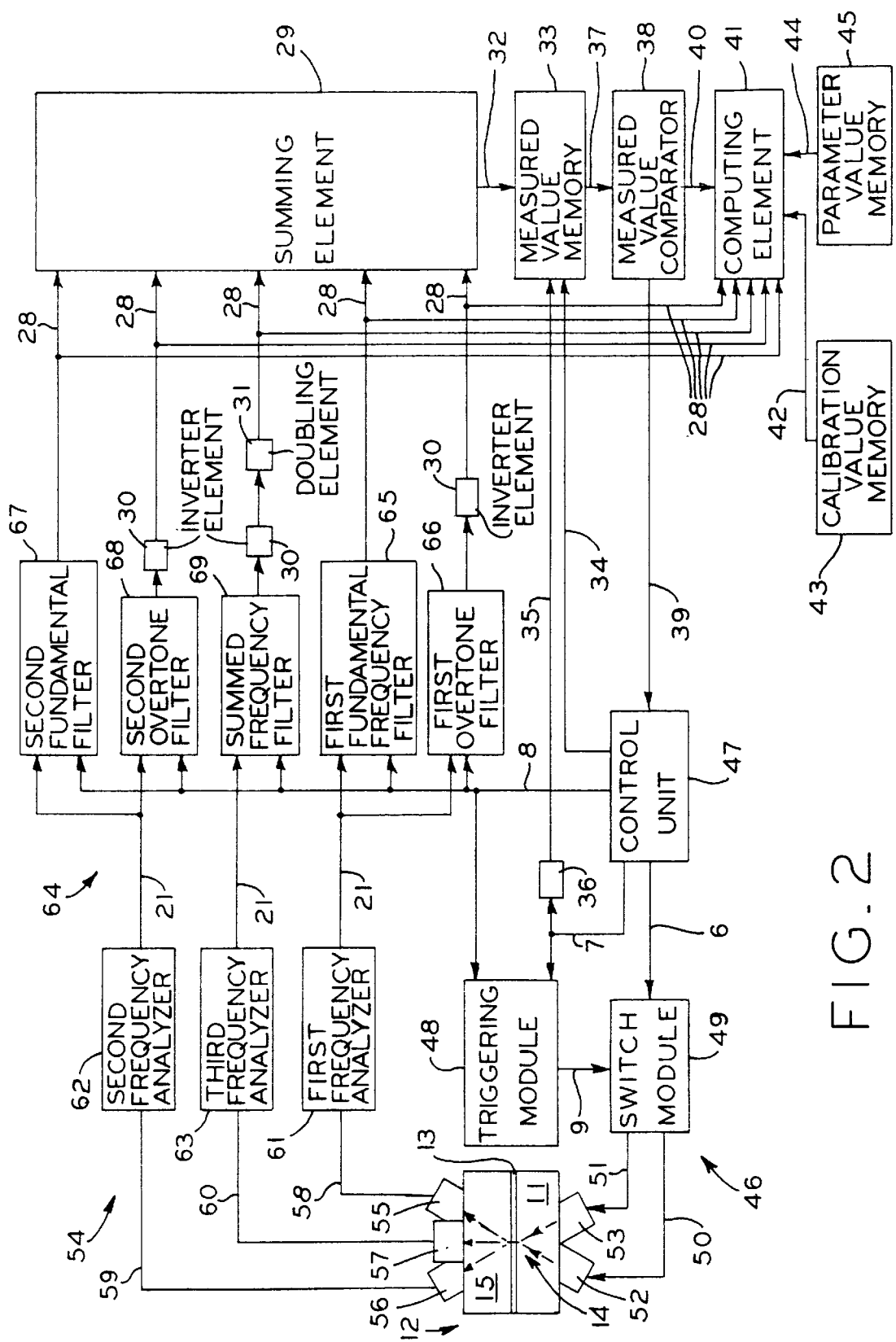

Additional advantageous configurations and advantages of the invention are the subject of the subclaims as well as of the following description of embodiment examples with reference to the figures of the drawing. The figures show:

FIG. 1 A block diagram of an embodiment example of a device for investigation of boundary layer areas using ultrasound with a transmission unit and a receiving unit having a transmission head and a receiving head, respectively, and FIG. 2 An additional embodiment example of a device for the investigation of boundary layer areas using ultrasound with a transmission unit and a receiving unit having several transmission heads and several receiving heads, respectively.

FIG. 1 shows in a block diagram an embodiment example of a device for investigation of boundary layer areas using ultrasound which has a central control unit 1. Connected to control unit 1 are a trigger module 2 and a switch module 3 with a transmission head 4 connected behind it forming a monofrequency transmission unit 5. The repetition frequency, the duration, the sole fundamental frequency in this embodiment, and the amplitude of a transmission signal which can be emitted by transmission head 4 within a measurement cycle progressively beginning from a relatively low initial value can be set with control unit 1.

The values for the repetition frequency and the duration can be transferred through a pulse line 6 to switch module 3. The values for the amplitude and the fundamental frequency of the transmission signal can be transferred through an amplitude line 7 and a frequency line 8 to trigger module 2. Using trigger module 2, a continuous wave train can be generated at the fundamental frequency provided and with amplitudes which can be variously set, which wave train can be further conducted over a trigger line 9 to switch module 3. With switch module 3, triggering transmission signals pulsed at the set repetition frequency and duration can be transmitted through a transmission line 10 to transmission head 4.

In the embodiment example depicted in FIG. 1, a transmission head 4 is provided with which the longitudinal waves for determination of tensile adhesive strength, or in a variation for determination of the shear adhesive strength, transverse waves can be generated, in each case striking perpendicularly. As represented in FIG. 1, transmission head 4 is linked to an initial adhesive piece 11 of a test body 12 such that a boundary layer area 14 formed, for example, by a bonding agent 13 between first adhesive piece 11 and a second adhesive piece 15 of test body 12 can be penetrated perpendicularly with longitudinal ultrasound waves. The repetition frequency and duration of the transmission signal are matched to the thicknesses of adhesive pieces 11, 15 such that reflection signals and transmission signals can be separated by time.

Across from transmission head 4 according to FIG. 1, a receiving head 16 of receiving unit 17 is connected to the second adhesive piece 15. Receiving head 16 has a bandwidth with which the fundamental frequency given off by transmission head 4 as well as at least frequency portions of the associated second harmonic as the lowest of the higher harmonics at the doubled fundamental frequency, which is generated through nonlinear reciprocal effects in the boundary layer area 14, can be detected as receiving signals.

Advantageously receiving head 16 has, for the purpose of increasing measuring precision, a frequency response with which the third, fifth, and sixth harmonics with three, five, and six times, respectively, the fundamental frequency can be detected as receiving signal.

The output signal of receiving head 16 can be fed through a receiving line 18 to a frequency analyzer 19 of receiving unit 17. With frequency analyzer 19, the Fourier spectrum of the receiving signal picked up by receiving head 16 can be generated. The output signal of frequency analyzer 19 can be fed into a compensation element 20 of receiving unit 17 with which the frequency amplitudes of the frequency portions of the receiving signals fed into frequency analyzer 19 which are distorted as a result of the frequency response of receiving head 16 can be compensated to a frequency-dependent sensitivity.

In one variant, receiving head 16 has a frequency response which is implicitly weighted for the frequency amplitudes according to the formation of the measured value described further below. In this variant, compensating element 20 depicted in FIG. 1 is not absolutely required.

The output signal of compensating element 20 or, in the variant without compensating element 20, the output signal of frequency analyzer 19 can be fed through frequency compensator lines 21 into a fundamental frequency filter 22, an initial overtone filter 23, a second overtone filter 24, a third overtone filter 25, and a fourth overtone filter 26 of an analysis unit 27. Fundamental frequency filter 22 as well as overtone filters 23, 24, 25, 26 are configured as bandpass filters which can be set with respect to their transmission frequency by means of control unit 1 through frequency line 8.

Fundamental frequency filter 22 is tuned to the—in this embodiment example—single fundamental frequency of the transmission signal. The transmission frequency of first overtone filter 23 is tuned to a frequency value belonging to a second harmonic associated with double the fundamental frequency. The transmission frequency of second overtone filter 24 is tuned to a frequency value corresponding to a threefold fundamental frequency of the third harmonic. The transmission frequency of third overtone filter 25 is matched to a frequency value of the fifth harmonic belonging to the fivefold fundamental frequency. The transmission of fourth overtone filter 26 is set up such that the frequency component of the sixth harmonic with sixfold fundamental frequency can be filtered out. Direct voltage components in the receiving signals bar thus eliminated.

The output signals of fundamental frequency filter 22 and of second overtone filter 24 and third overtone filter 25 corresponding to the frequency amplitudes at the corresponding transmission frequencies can be fed through monofrequency lines 28 into a summing element 29 of evaluation unit 27. With summing element 29, the frequency amplitudes which are fed in can be summed into a measured value. The output signals of first overtone filter 23 as well as that of fourth overtone filter 26 can be fed into summing element 29 through an inverter element 30 connected upstream of each with downstream doubling element 31 as signal converter over monofrequency lines 28. With one inverter element 30 and downstream doubling element 31 for each, the frequency amplitude of the upstream overtone filter 23, 26 of each is provided with a negative sign and is doubled.

The measured value formed from the unweighted positive and/or doubly weighted negative frequency amplitudes can be fed through a summing signal line 32 to a measured value input of a measured value memory 33. In addition, a clock signal from control unit 1 which repeats periodically with the repetition rate of the transmission signal can be fed to measured value memory 33 through a clock line 34. Finally, an amplitude value—preferably proportional to the amplitude of the transmission signal—which can be generated in an amplitude converter 36 connected to amplitude line 7 can be fed to measured value memory 33 through an amplitude line 35. In measured value memory 33 the measured values with respect to the amplitude of the transmission signal can be calibrated with the repetition frequency of the clock signal, which measured values can be fed to a two-stage measured value comparator 38 through an output line 37.

In two-stage measured value comparator 38, two successive calibrated measured values can be stored and, by way of example, compared through subtraction or division. If the current calibrated measured value is larger than the preceding calibrated measured value, a step signal for increasing the amplitude of the transmission signal can be fed to control unit 1 through a step control line 39. If, on the other hand, the current calibrated measured value is smaller than the preceding calibrated measured value, a stop signal can be directed to control unit 1 through step signal line 39 to terminate the measurement cycle.

In addition, each calibrated measured value which is directed to measured value comparator 38 can be fed through a measured value output line 40 to a computing element 41 of analysis unit 27 to which computing element the individual frequency amplitudes can continue to be fed separately by way of various monofrequency lines 28. Computing element 41 is connected by means of a calibrated value line 42 to a calibrated value memory 43 and by means of a parameter line 44 to a parameter value memory 45.

With computing element 41, the cohesive force relationships as well as adhesion in the boundary layer area 14 of test body 12 which is being investigated can be determined from the calibrated measured values formed using summing element 29, the individual values of the frequency amplitudes, and parameter values filed cumulatively or alternatively with calibrated values stored in the calibrated value memory 43 and/or parameter values stored in the parameter memory. The calibrated values recorded from the calibration sample and stored in the calibration value memory 43 serve as phenomenological reference and the parameter values stored in the parameter value memory 45 serve as input data for a model of boundary layer 14 of test body 12 calculated on the basis of the elasticity formulas.

FIG. 2 shows in a block diagram a further example of a device for investigating boundary layer areas with ultrasound. The embodiment example represented in FIG. 2 has a series of components which have already been described in detail in connection with the embodiment example of FIG. 1. These components are provided with the same reference numbers as for the embodiment example explained using FIG. 1 and are not further explained below.

The device according to FIG. 2 has a multifrequency transmission unit 46 in which two triggering transmission signals with differing first and second fundamental frequency can be generated by means of a control unit 47, a triggering module 48, and a switch module 49 which are wired according to the embodiment example explained in connection with FIG. 1. The trigger signals can be fed through a first transmission line 50 and a second transmission line 51, respectively, to a first transmission head 52 and a second transmission head 53, respectively, with transmission characteristic adjusted to the respective fundamental frequencies. In the depiction according to FIG. 2, transmission heads 52, 53 are connected to first adhesive piece 11 of test body 12.

In the case of dual-frequency or multiple frequency radiation, oblique radiation is generally required for geometrical reasons. For determination of the tensile adhesive strength, the displacement components perpendicular to the boundary layer area, and for determination of shear adhesive strength, displacement components parallel to the boundary layer area are evaluated from longitudinal waves and transverse waves beamed with the transmission heads 52, 53 in the embodiment example according to FIG. 2.

The device represented in FIG. 2 has a receiving unit 54 which has a first receiving head 55, a second receiving head 56, and a third receiving head 57. First receiving head 55 is adjusted with respect to transmission head 52 which is assigned to it and is provided with a bandwidth such that a first receiving signal with the first fundamental frequency as well associated second harmonic with double the frequency of the first fundamental frequency are detectable. In addition, the first receiving head 55 has a frequency response with which the frequency components of the second harmonic of the first fundamental frequency is detectable with a double intensity as compared with a frequency-independent uniform characteristic.

The second receiving head 56 is appropriately adjusted with respect to the second transmission head 53 assigned to it and has a frequency response which allows the detection of the second fundamental frequency as well as the second harmonic [nominative or objective; I believe that it should be in the genitive as is "the second fundamental frequency"] of the second fundamental frequency with double intensity.

Lastly, the third receiving head 57 is adjusted to transmission heads 52, 53 and is provided with bandwidth such that a receiving signal generated on the basis of nonlinear reciprocal reactions in the boundary layer area 14 struck by the transmission signals of transmission heads 52, 53 with a frequency component corresponding to the summed frequency of the first fundamental frequency and the second fundamental frequency can be detected. The third receiving head 57 has a frequency response which, in the range of a summed frequency formed additively from the first fundamental and the second fundamental, has a sensitivity which corresponds to the sensitivity of the first receiving head 55 and to the sensitivity of the second receiving head 56 at the first fundamental and the second fundamental, respectively.

The receiving signals of first receiving head 55, second receiving head 56, and third receiving head 57 can be fed through an assigned first receiving line 58, second receiving line 59, and a third receiving line 60, respectively, to a first frequency analyzer 61, a second frequency analyzer 62, and a third frequency analyzer 63 of receiving unit 54.

The device according to FIG. 2 has an analysis unit 64 which has a first fundamental frequency filter 65 and a first overtone filter 66 which are each configured as bandpass filters and which are connected to the first frequency analyzer 61 through frequency component line 21. With the first fundamental frequency filter 65 of the first frequency analyzer 61, the frequency amplitude at the first fundamental frequency can be filtered out of the output signal. With the first overtone filter 66, the frequency component of the second harmonic with double the value of the first fundamental frequency can be filtered out.

In addition, analysis unit 64 has a second fundamental filter 67 and a second overtone filter 68 which are connected through a frequency component line 21 to the second frequency analyzer 62 and are likewise designed as controllable bandpass filters. From the output signal of the second frequency analyzer 62, the filter component corresponding to the second fundamental frequency can be filtered out with the second fundamental filter 67, and the frequency component corresponding to the second harmonic with double the second fundamental frequency can be filtered out with the second overtone filter 68. The output signals of fundamental frequency filters 65, 67 can be fed directly to summing element 29 of analysis unit 64, and the output signals of overtone filters 66, 68 after reversal of the sign by inverting element 30 can be fed into summing element 29 through the respective monofrequency lines 28.

Finally, analysis unit 64 is provided with a summed frequency filter 69 which is connected through a frequency component line 21 to the third frequency analyzer 63, with which summed frequency filter a frequency component in the range of a summed frequency value formed additively from the first fundamental frequency and the second fundamental frequency can be filtered out. The output signal of summed frequency filter 69 can be fed, after reversal of the sign through an inverting element 30 and doubling through a doubling element 31, to the summing element 29 through a monofrequency line 28.

With summing element 29, the frequency amplitudes weighted partially through the frequency response of receiving heads 55, 56, 57 and partially through the doubling element 31 and inverting elements 30 can be joined additively into measured values which can be fed into the measured value memory 33 through the summing signal line 32 for further processing corresponding to the embodiment example explained with reference to FIG. 1. In the embodiment example explained using FIG. 2, it is advantageous for the individually detected frequency components to be free of overlap so that the possibility of an overlay of receiving signals elicited through various physical processes can be to the greatest extent possible excluded in the frequency range.

Through radiation of at least two fundamental frequencies into test body 12 as well as detection of frequency components in the fundamental frequencies, the associated second harmonics and in the summed frequency from the fundamental frequencies, an increase in the measuring precision and informative value can be assured.

An additional improvement is, by way of example, created corresponding to the embodiment example explained using FIG. 2 through higher harmonics both of the fundamental frequencies as well as of the summed frequencies being detected and being used in the formation of the measured value.

In a further embodiment example of a device for the investigation of boundary layer areas 14 with ultrasound, it is provided that an arrangement of transmitting heads be used with which both longitudinal as well as transverse waves can be generated.

What is claimed is:

1. An apparatus for investigating boundary layer areas with ultrasound, said apparatus comprising:

a transmitter for generating transmission signals which have adjustable amplitudes and a fundamental frequency, said transmission signals having frequency amplitudes;

a receiver coupled to said transmitter for detecting transmission signals at one of said fundamental frequency and a lowest associated higher harmonic frequency of said fundamental frequency, and for detecting the frequency amplitudes of said transmission signals;

an analyzer coupled to said receiver having a summing element for combining selected frequency amplitudes of the detected transmission signals into a measured value, said measured value including the fundamental frequency amplitude and double the negative value of the associated lowest higher harmonic frequency amplitude; and a filter coupled to said analyzer for detecting one of said fundamental frequency and a lowest associated higher harmonic frequency amplitude and for suppressing direct current components.

2. Apparatus according to claim 1 wherein the measured value includes the frequency amplitude of the associated third harmonic of the fundamental frequency.

3. Apparatus according to claim 1 wherein the measured value includes the frequency amplitude of the associated fifth harmonic of the fundamental frequency.

4. Apparatus according to claim 1 wherein the measured value includes a component value of double the negative value of the frequency amplitude of the sixth harmonic of the fundamental frequency.

5. Apparatus according to claim 1 wherein the transmission signal has two fundamental frequencies.

6. Apparatus according to claim 5 wherein the measured value includes the frequency amplitude at the summed frequency of the two fundamental frequencies.

7. Apparatus according to claim 5 wherein the measured value includes the frequency amplitude of one of the summed frequencies and the difference frequencies of the fundamental frequencies, higher harmonics of the fundamental frequencies, and combinations thereof.

8. Apparatus according to claim 1 including a doubling signal converter for the value of the lowest higher harmonic frequency amplitude.

9. Apparatus according to claim 1 wherein the frequency response of the receiver is set to double the intensity of a corresponding frequency amplitude.

10. Apparatus according to claim 1 wherein said transmitter generates longitudinal waves.

11. Apparatus according to claim 1 wherein said transmitter generates transverse waves.

12. Apparatus according to claim 1 wherein said transmitter generates longitudinal and transverse waves.

13. Apparatus according to claim 1 wherein said analyzer includes a calibrated value memory with which the measured value can be converted using empirically-obtained calibrated values as absolute force values in investigated boundary layer areas.

14. Apparatus according to claim 1 wherein the analyzer includes a parameter value memory in which parameter values are stored by means of which, in combination with the measured values, absolute force values in investigated boundary layer areas are computed.

* * * * *

UNITED STATES PATENT AND TRADEMARK OFFICE
CERTIFICATE OF CORRECTION

PATENT NO. : 6,164,136
DATED : December 26, 2000
INVENTOR(S) : Sigrun Hirsekorn and Silvia Fassbender It is certified that error appears in the above-identified patent and that said Letters Patent are hereby corrected as shown below:

In the Abstract, Line 1, change "lazier" to --layer--

Signed and Sealed this

First Day of May, 2001

Attest:

NICHOLAS P. GODICI

Attesting Officer     Acting Director of the United States Patent and Trademark Office